United States Patent [19]
Yacowitz

[11] Patent Number: 5,401,242
[45] Date of Patent: Mar. 28, 1995

[54] APPARATUS FOR INJECTING A SUBSTANCE INTO THE SKIN

[76] Inventor: Harold Yacowitz, 221 Second Ave., Piscataway, N.J. 08854

[21] Appl. No.: 997,235

[22] Filed: Feb. 25, 1993

[51] Int. Cl.6 ............................................. A61M 31/00
[52] U.S. Cl. ...................... 604/48; 604/289; 606/186
[58] Field of Search ...................... 608/289, 22, 47, 46, 608/48; 606/186, 169, 116, 172; 81/9.22

[56] References Cited

U.S. PATENT DOCUMENTS

| | | | |
|---|---|---|---|
| 464,801 | 12/1891 | O'Reilly | 81/9.22 |
| 1,767,469 | 6/1930 | Metzner | 81/9.22 |
| 4,159,659 | 7/1979 | Nightingale | 81/9.22 |
| 4,204,438 | 5/1980 | Binaris et al. | 81/9.22 |
| 4,286,599 | 9/1981 | Hahn et al. | 606/116 |
| 4,771,660 | 9/1988 | Yacowitz | 81/9.22 |
| 5,054,339 | 10/1991 | Yacowitz | 606/186 |

FOREIGN PATENT DOCUMENTS 269164  6/1988  European Pat. Off. ............. 606/186

*Primary Examiner*—John G. Weiss
*Attorney, Agent, or Firm*—Robert A. Green

[57] ABSTRACT

Apparatus for injecting a substance into the skin including vibrating means and a hollow needle coupled thereto and receiving an injectable substance from a source thereof coupled into the open end thereof. A peristaltic pump pumps the substance to the tattoo needle. A tattooing guide is secured to the apparatus for controlling the depth of the operation.

8 Claims, 2 Drawing Sheets

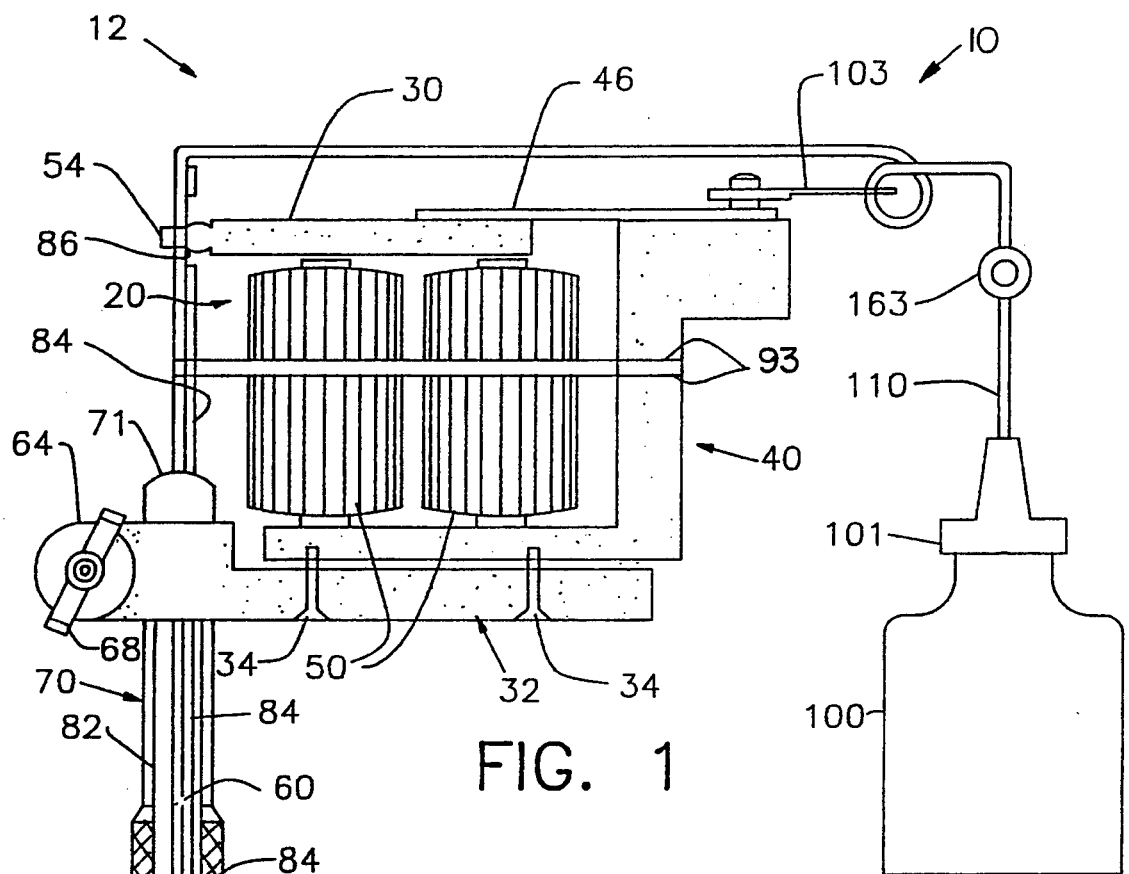
FIG. 1
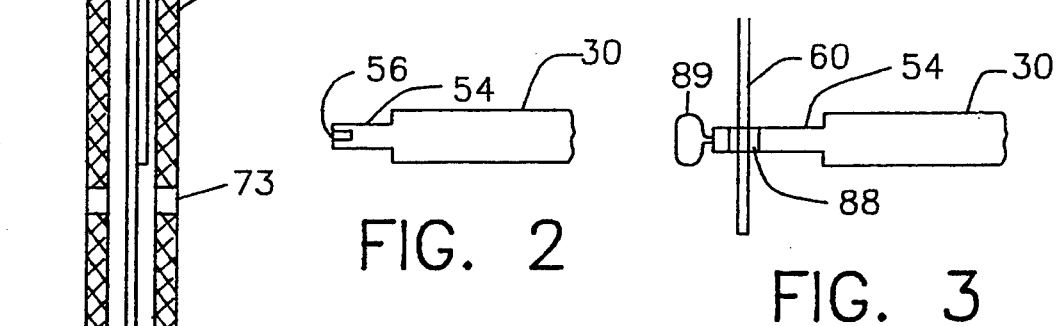
FIG. 2
FIG. 3
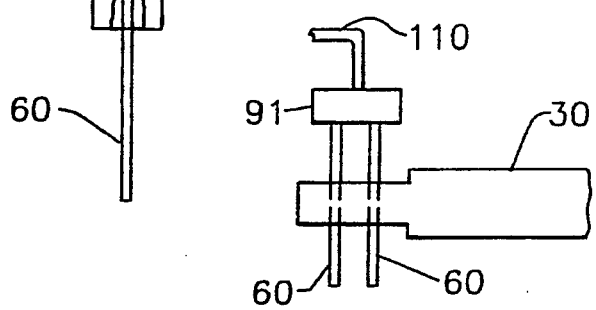
FIG. 4
FIG. 5

APPARATUS FOR INJECTING A SUBSTANCE INTO THE SKIN

BACKGROUND OF THE INVENTION

This invention relates to the delivery of substances, into the skin, particularly substances such as drugs, vaccines, biologicals and the like. Single needle syringes are used for this purpose, however, such devices are limited in their utility when it is desired to deliver medical substances into a relatively large area on the skin. In addition there is little control of these devices.

Another device which has great utility for injecting substances into the skin is a tattooing machine. Such an apparatus, particularly a tattooing machine embodying the present invention, would be useful for the known application of injecting pigment into the skin but it would be particularly useful for injecting medical substances into the skin.

In the past, tattooing apparatus used needles comprising solid metal pins or solid metal points on pins for performing the injecting function. Usually several such solid pins were soldered together and they were used by being dipped periodically into the medication or pigment to be injected. In this procedure, capillary action causes the medication or pigment to be drawn up along the needles and sufficient material cannot always be readily provided in this way for good results.

In addition, spaces are present between the tips of the pins of a group and tissue debris from the epidermis can collect therein.

This procedure and apparatus was improved, as described and claimed in U.S. Pat. No. 5,054,339 of Dr. Harold Yacowitz, by the provision of a source of pigment coupled by a plastic tube to the tips of the tattoo needles or needle assembly so that the periodic dipping procedure was not required. While this method and apparatus operate satisfactorily and represent a considerable improvement over the prior art, the preparation of the apparatus for use may be moderately time consuming. Also, the problems inherent in the use of solid tattoo needles are present.

Another problem affecting the operation of tattooing apparatus of the past arose from the need for the injected material to reach a uniform depth under the skin and for this the operator had to try to hold the tattoo machine a constant distance from the skin. If he could do this, he could obtain the proper depth of needle penetration. However, it is almost impossible to maintain this constant distance by eye, with the result that the injected material often reached varying depths. If this occurred with pigment, bleeding and pain might be caused or fading of the tattoo might result if the tattoo was not done to a sufficient depth.

SUMMARY OF THE INVENTION

The injection apparatus of the invention uses a hollow needle for directing medication, pigment or the like into the skin and, in addition, a guide is provided to control automatically the exact depth of penetration of the injection needle into the skin.

The many advantages of the invention are set forth below.

DESCRIPTION OF THE DRAWINGS

FIG. 1 is a side elevational view of apparatus embodying the invention;

FIG. 2 is a plan view of a portion of the apparatus of FIG. 1;

FIG. 3 is a side, elevational view in section of a modification of a portion of the invention;

FIG. 4 is a side elevational view of a modification of a portion of the invention;

FIG. 5 is a sectional elevational view of a modification of a portion of the invention;

DESCRIPTION OF THE INVENTION

Figure 6:
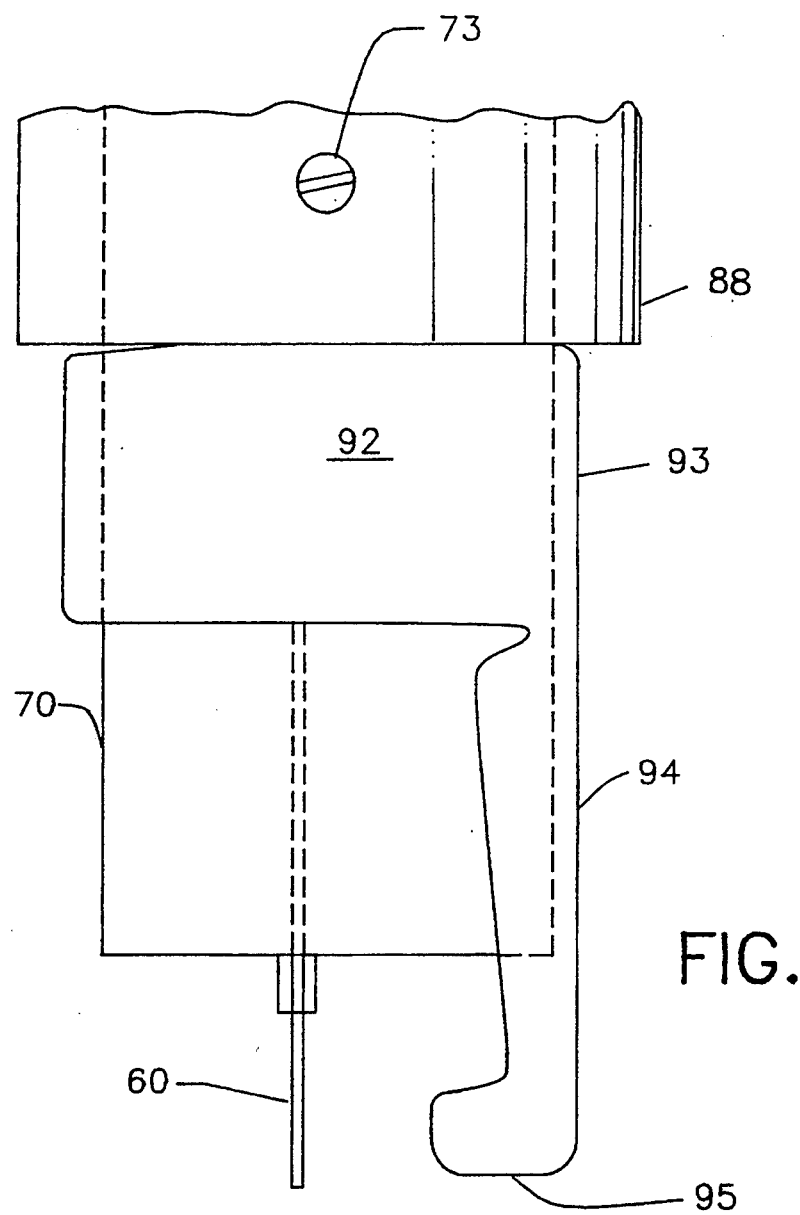
FIG. 6 is a side elevational view of a modification of the invention.

Apparatus embodying the present invention is used to inject a substance such as tattooing pigment, medication or similar materials into the skin of humans or animals. The apparatus may use some of the tattooing apparatus described and claimed in U.S. Pat. Nos. 4,771,660 and 5,054,339.

Since all of the features of a working tattooing apparatus are shown in these two patents, all may not be shown herein.

Tattooing apparatus 10 embodying the invention includes a needle and needle holder assembly 12 including a vibrator made up of a U-shaped housing 20 including an upper leg or bar 30, a lower leg 32 and a connecting L-shaped leg 40. The leg 32 is secured to L-shaped leg 40 by means of two countersunk screws 34 or in any other suitable fashion. The upper leg 30 is the vibrating portion of the armature and it includes a rearwardly projecting spring-like metal strip 46 which secures the bar 30 to the side leg 40. Electrical coils 50 are mounted on the housing 20 for use in causing the upper bar 30 to vibrate and move up and down and drive the tattoo needle, to be described, up and down.

The leading end portion 54 of the upper leg of bar 30 has a vertical slot 56 (FIG. 2) for receiving and coupling to a tattoo needle. The leading end of the lower leg 32 is formed with a horizontally disposed split ring 64 which is adapted to receive a needle holder 70 and carries a threaded wing nut 68 for securing the needle holder therein.

The needle holder 70 comprises a rigid, hollow metal tube having a longitudinal slot 82 in its wall extending from the upper end 71 of the tube 70 to near the lower end. A tattooing needle 60 is seated in the slot 82 in tube 70 and is accessible at the lower end thereof to perform its tattooing function. A knurled adjustable sleeve 72, which serves as a grip for the operator of the apparatus, is slidably mounted on the needle holder 70 and is secured in place by one or more set screws 73.

Elastic bands 93 may be provided enclosing armature leg 40 and needle 60 to hold the needle securely in place.

According to the invention, the needle 60 which is used to administer pigment, medication or other substance, unlike needles in the prior art, is a hollow tube. This hollow tube may be of any suitable size and shape so that, unlike the clusters of solid needles used in the prior art, only a single needle is required, although more than one might be used under special circumstances. The hollow needle 60 may be of metal, if feasible, plastic or the like.

Since a hollow needle 60 may not be sufficiently rigid, especially when made of a plastic, a solid metal reinforcing rod or bar 84 is soldered or otherwise secured to the needle 60. The solid bar 84 extends along a suitable portion of the length of the needle from near the upper end of the needle where the needle is coupled to the armature bar 30. At its upper end, the solid bar 84 has an opening 86 into which the slotted member 54 can enter to engage the needle and place the hollow needle 60 in the slot 56.

The tattooing apparatus 10 is operated in conjunction with a container 100 of pigment, medication or the like. The container 100 has a threaded cap 101 which has a small hole into which is inserted a length of flexible tubing 110 which extends through a micro-peristaltic pump 163 to the upper open end of the tattoo needle 60 into which it is inserted. In the past, if anyone considered using a hollow needle tattooing needle, he could not do so because there was no way to feed pigment to the needle. This problem is solved by the present invention.

If desired, an apertured tab 103 is secured to the armature housing or other convenient location to guide the tubing to the needle 60.

If desired, the needle 60 can extend through a hole 88 in the portion 54 of armature leg 30 and it can be held in place by a set screw 89 as illustrated in FIG. 3. The method of attachment described above is preferred because it permits rapid removal and changing of needles.

In addition as shown in FIG. 4, under some circumstances, it may be desirable to utilize a plurality of hollow needles 60 having a manifold 91 coupled to their upper inlet ends for receiving the tubing 110. Also, a combination of solid and hollow needles might be used under some circumstances as shown in FIG. 5.

The above-identified U.S. Pat. No. 5,054,339 shows and describes electronic circuitry for controlling the operation of the pump 163.

Figure 7:
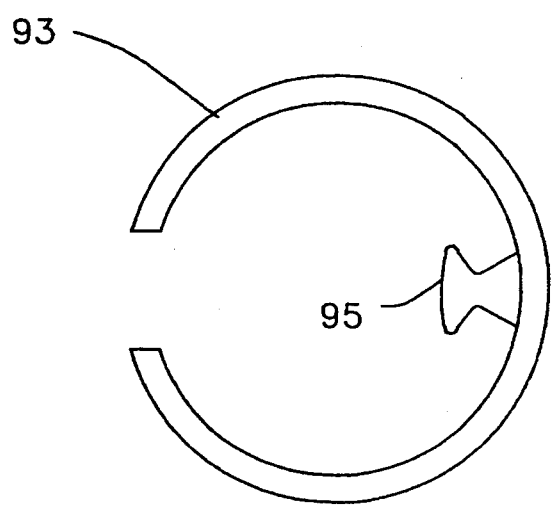
FIG. 7 is a plan view of a portion of the invention.

In a modification of the apparatus 10 shown in FIGS. 6 and 7, a needle and tattooing guide 92 is coupled to the rigid needle holder 70. The guide is made of a resilient material, such as spring steel, Teflon or the like and includes an annular collar portion 93 which engages the needle needle holder 70 and a vertical arm 94 which extends downwardly therefrom and terminates in a foot 98 which can rest on the skin being tattooed. The upper end of the guide 92 bears against the lower end of the sleeve or grip 72.

To locate the guide 92 on needle tube 70 with respect to the tattooing needle 60, the wing nut 68 and the knurled sleeve is loosened so that it can be adjusted up or down and the operator presses on the armature bar 30 and this presses on the needle to fully extend the tip of the needle 60 out of the bottom of needle holder 70. Then the guide 92 is moved up or down until the tip of the needle is at the desired location with respect to the foot of the needle guide. The relationship between the foot of the needle guide and the tip of the needle is readily determined by those skilled in the art and is determined by the desired depth of the tattooing needle. With the guide bearing against the lower end of grip 72, the grip is locked in place and wing nut 68 is tightened.

Some of the advantages of the invention are as follows:

1. The hollow needle allows delivery of pigment, medication or the like directly into the tattoo site. This results in darker tattoos and more precise delivery of pigment or medication.

2. The hollow needle does not have to be removed from the tattoo gun in order to attach the plastic pigment or medication delivery tube to it. This speeds up the procedures for changing needles.

3. By coupling the needle directly to the source of fluid, sterility of the fluid can more easily be maintained.

4. If the plastic delivery tubing should be inadvertently pulled off the tup of the needle, it can be put back in place without removal of the needle from the needle tube.

5. Since the hollow needle carries pigment inside the needle, there is no need to use clusters of solid pins to achieve tattoos of different widths. Simply using a different diameter needle will achieve wider or narrower lines.

6. The hollow single needle does not accumulate tissue debris.

7. The needle guide resting on the skin permits the achievement of constant uniform penetration of the epidermis and/or the dermis and this provides more uniform tattoos or delivery of medication.

8. Since, with the guide, the operator is not required to hold the tattooing apparatus above the skin and try to achieve uniform penetration visually, the operator can use the apparatus more easily and without fatigue for a longer period of time than in the past.

What is claimed is:

1. Apparatus for delivering a liquid substance into skin comprising
    a skin penetrating needle having an operating end adapted to penetrate the skin of a subject and an open end for receiving a fluid to be injected into a subject,
    said skin penetrating needle comprising a hollow tube,
    a source of fluid to be injected,
    a supply tube coupled from said source of fluid to said open end of said skin penetrating needle,
    a pump coupled to said supply tube for providing generally continuous flow and controlling the flow of fluid from said source to said open end of said needle, and
    a vibrator coupled to said needle for moving the needle up and down so that it can enter the skin,
    said apparatus being adapted to be held in the hand of an operator and positioned adjacent to the skin to be injected with said needle closely adjacent to said skin so that it enters the skin under the control of said vibrator.

2. The apparatus defined in claim 1 and including a strengthening rod secured to said hollow needle.

3. The apparatus defined in claim 1 wherein said pump is a peristaltic pump.

4. The apparatus defined in claim 1 wherein said skin penetrating needle is a first needle
    a second skin penetrating needle in operative relation with said first skin penetrating needle, and
    a fluid supply manifold coupled to said first and second skin penetrating needles and supplying injectable fluid there.

5. The apparatus defined in claim 1 and including at least one solid skin penetrating needle in operative relation with said skin penetrating needle which is a hollow tube.

6. Apparatus for delivering a liquid substance into the skin comprising
    a needle tube for carrying a needle used for injecting a substance into the skin,
    a slidable sleeve enclosing said needle tube and having an outer surface grasped by an operator of said apparatus, a vertical slot in said needle tube and said slidable sleeve for permitting a needle to be inserted into said needle tube, said needle tube having an upper end and a lower end and said needle extending beyond the upper and end of said needle tube and below the lower end of said needle tube, a vibrator coupled to said needle to drive it up and down to perform its skin injection operation, said needle comprising a hollow tube and having an upper end and a lower end, a container of a substance to be injected into the skin, a flexible feed tube coupled from said container to the upper end of said needle, and a peristaltic pump coupled to said flexible feed tube and operable to feed fluid in said feed tube to said needle, said apparatus being held in the hand with said needle adjacent to skin to be injected with said vibrator causing said needle to enter the skin under the control of the operator.

7. The apparatus defined in claim 6 and including an electrical vibrator means slidably secured to said needle tube and coupled to said needle for vibrating said needle.

8. The apparatus defined in claim 6 and including guide secured to said needle tube adjacent to the operating end of said needle, said guide including an annular sleeve which engages said needle tube and a depending portion which extends downwardly from said annular sleeve and includes a foot which engages the skin of the subject.

* * * * *